US008287846B2

(12) United States Patent
Rampoldi et al.

(10) Patent No.: US 8,287,846 B2
(45) Date of Patent: Oct. 16, 2012

(54) COSMETIC OR DERMATOLOGICAL PREPARATIONS COMPRISING N-ACETYLCYSTEINE

(75) Inventors: Luca Rampoldi, Lainate (IT); Alberto Moretto, Ponte San Nicolo (IT); Alessandro Grassano, Monza (IT)

(73) Assignee: ZAMBON S.p.A., Bresso (IT)

( * ) Notice: Subject to any disclaimer, the term of this patent is extended or adjusted under 35 U.S.C. 154(b) by 540 days.

(21) Appl. No.: 12/374,828

(22) PCT Filed: Jul. 13, 2007

(86) PCT No.: PCT/EP2007/057271
§ 371 (c)(1),
(2), (4) Date: Apr. 9, 2009

(87) PCT Pub. No.: WO2008/012220
PCT Pub. Date: Jan. 31, 2008

(65) Prior Publication Data
US 2010/0021399 A1  Jan. 28, 2010

(30) Foreign Application Priority Data
Jul. 25, 2006  (EP) .................................. 06015440

(51) Int. Cl.
| | | |
|---|---|---|
| A61K 31/74 | (2006.01) | |
| A61K 8/18 | (2006.01) | |
| A61K 8/02 | (2006.01) | |
| A61K 31/70 | (2006.01) | |
| A61K 47/30 | (2006.01) | |
| A61Q 17/04 | (2006.01) | |
| A61L 9/00 | (2006.01) | |
| B01D 53/34 | (2006.01) | |
| A01N 65/00 | (2009.01) | |
| A01N 43/04 | (2006.01) | |
| A01N 37/12 | (2006.01) | |
| A01N 33/08 | (2006.01) | |

(52) U.S. Cl. ..................... 424/78.03; 424/59; 424/76.21; 424/401; 424/725; 514/23; 514/558; 514/562; 514/665; 514/785; 514/847; 514/861; 514/862; 514/863; 514/864; 514/937; 514/939; 514/941; 514/943; 514/947; 560/1; 560/129; 560/147; 560/182; 560/198

(58) Field of Classification Search ............... 424/78.03, 424/59, 76.21, 401, 725; 514/23, 558, 562, 514/665, 785, 847, 861, 862, 863, 864, 937, 514/939, 941, 943, 947; 560/1, 129, 147, 560/182, 198
See application file for complete search history.

(56) References Cited

U.S. PATENT DOCUMENTS

| | | | |
|---|---|---|---|
| 4,708,965 A | * | 11/1987 | Morgan ........................ 514/563 |
| 5,691,380 A | | 11/1997 | Mason et al. |
| 5,733,535 A | | 3/1998 | Hollingshead et al. |
| 5,879,666 A | | 3/1999 | Lucas et al. |

FOREIGN PATENT DOCUMENTS

| | | |
|---|---|---|
| EP | 1 006 993 | 10/2004 |
| EP | 1 570 840 | 9/2005 |
| FR | 2 675 046 | 10/1992 |
| JP | 2004 217 589 | 8/2004 |
| WO | 93 04669 | 3/1993 |
| WO | 95 00136 | 1/1995 |
| WO | 95 34280 | 12/1995 |
| WO | 96 00060 | 1/1996 |

OTHER PUBLICATIONS http://en.wikipedia.org/wiki/Ester; material taken from definitions in references of 1997 and 1848; downloaded on Jan. 3, 2012.*
"Ester", Wikipedia [online], [Retrieved Jul. 11, 2012] Retrieved from the Internet: <URL: http://en.wikipedia.org/wiki/Ester>.*
"Polyglyceryl Esters", Cyberlipid [online], [Retrieved Jul. 11, 2012] Retrieved from the Internet: <URL: http://www.cyberlipid.org/glycer/glyc0013.htm>.*

* cited by examiner

*Primary Examiner* — Richard Schnizer
*Assistant Examiner* — Jane C Osweki
(74) *Attorney, Agent, or Firm* — Oblon, Spivak, McClelland, Maier & Neustadt, L.L.P.

(57) ABSTRACT

The present invention relates to odour improved dermatological or cosmetic preparations comprising N-acetylcysteine and a polyol system containing one or more polyols as masking odour agents. The emulsions of the present invention are useful in the treatment of dermatological disorders or cosmetic skin conditions.

13 Claims, No Drawings

COSMETIC OR DERMATOLOGICAL PREPARATIONS COMPRISING N-ACETYLCYSTEINE

The present invention relates to odour-improved cosmetic or dermatological preparations for topical use comprising N-acetylcysteine.

N-acetylcysteine (hereinafter referred to also as NAC) is a safe drug practically without adverse effects, mainly known as mucolytic agent.

Furthermore NAC has been reported to be an active agent for treating several additional diseases and conditions including skin conditions such as wrinkles, spots and other histological changes associated with skin aging or associated with the exposure to extrinsic factors; and skin diseases such as pathologies including hypercheratosis and diseases mediated by proteases (see, for example, WO9500136), psoriasis, xerosis, ichtyosis, palmar hypercheratosis and plantar hypercheratoses (see, for example, EP1570840).

However the unpleasant sulphur odour exhaled by N-acetylcysteine and its chemical instability create problems for the topical use of preparations containing it.

Many efforts for controlling release of malodorous sulphur compounds in compositions containing N-acetylcysteine have previously been made. U.S. Pat. No. 5,733,535 describes the use of conventional chelating agents such as zinc salts to reduce development of malodour arising from N-acetylcysteine and its thiol and hydrogen sulphide degradation products. Various attempts to minimize the level of malodour by using fragrances and combination of specific chemical perfumes as odour masking materials have been also made. The use of zinc or zinc derivatives to eliminate malodour associated with N-acetylcysteine is also described in WO9304669, WO9534280 and WO9600060.

The problem of reducing or removing unpleasant odour from compositions containing N-acetylcysteine has been faced, in U.S. Pat. No. 5,691,380, by using a silicon-based emulsion system. Furthermore, the use of cyclodextrines as odour absorbing compounds is known (see, for example, EP1006993 and U.S. Pat. No. 5,879,666).

We have now found that the problem of malodour production associated with topical preparations containing N-acetylcysteine can be solved by adding a polyol system consisting of one or more polyols as odour controlling agents to said preparations.

It is therefore an object of the present invention to provide an odour-improved dermatological or cosmetic preparation for topical use, which comprises NAC and a physiologically acceptable carrier, characterized in that said preparation comprises a polyol system as odour controlling agent.

The term "polyol system" as used herein means one or more polyols selected from the group consisting of glycerol; glyceryl fatty acid esters, i.e. glycerol partially esterified with fatty acids selected from a fatty acid having a carbon number from 8 to 22 including octanoic (caprylic) acid, pelargonic acid, decanoic (capric) acid, dodecanoic (lauric) acid, myristic acid, palmitic acid, stearic acid, isostearic acid, oleic acid and linoleic acid; polyglyceryl fatty acid esters, i.e. polyglycerol having a degree of polymerization ranging from 3 to 10, preferably from 3 to 6, more preferably 3, partially esterified, preferably monoesterified, with fatty acids selected from saturated and partially unsaturated fatty acids having a carbon number from 8 to 20 including octanoic (caprylic) acid, nonanoic (pelargonic) acid, decanoic (capric) acid, dodecanoic (lauric) acid, tetradecanoic (myristic) acid, hexadecanoic (palmitic) acid, octadecanoic (stearic) acid, isooctadecanoic (isostearic) acid, cis-9-octadecenoic (oleic) acid, cis-9,12-octadecadienoic (linoleic) acid, eicosanoic (arachidic) acid, docosanoic acid (behenic) and cis-13-docosenoic acid (erucic acids); sugar polyalcohols selected from erythritol, xylitol, mannitol and sorbitol; and saccharides selected from dextrose, sucrose, lactose and maltodextrines.

Among the above glyceryl fatty acid esters, monoesters are preferred; monoesters with stearic acid, isostearic acid and oleic acid are more preferred, in particular glyceryl stearate and glyceryl oleate.

Among the above polyglyceryl fatty acid esters, monoesterified polyglycerol having a degree of polymerization of 3 to 6, particularly 3, are preferred; monoesters with stearic or isostearic acid are more preferred, polyglyceryl-2-diisostearate, diisostearyl-polygliceryl-3-diinolate and polyglyceryl-3-diisostearate are most preferred.

In a preferred aspect of the present invention, the polyol system is a polyglyceryl fatty acid ester, especially polyglyceryl-2-diisostearate, polyglyceryl-3-diisostearate or a mixture thereof. In another preferred aspect the polyol system is a combination of two, or more than two polyols; in a more preferred aspect the polyol system is a combination of one or more, preferably two, polyglyceryl fatty acid esters with one or more, preferably two, sugar polyalcohols as defined above; in a still more preferred aspect the polyol system is a combination of two polyglyceryl stearic or isostearic monoesters, particularly polyglyceryl-2-diisostearate and polyglyceryl-3-diisostearate and at least one saccharide as defined above, especially xylitol.

The polyol system is able not only to control unpleasant odours obtaining an odour improved preparation, but also to increase the stability of the preparation.

The term "to control/controlling" as used herein means that the polyol system is able to prevent/preventing, to reduce/reducing and/or to remove/removing malodour development from NAC preparations.

The term "odour improved" as used herein means that malodour exhaled by the NAC preparations is minimized or absent, especially regarding unpleasant sulphur odour.

The preparations are not necessarily odourless; if desired, fragrances and perfumes can be added.

The term "topical" as used herein means applied on the surface of the skin.

The term "physiologically acceptable" as used herein means compatible with the skin without undue toxicity, incompatibility, instability or allergic response.

The preparations of the present invention are in the form of emulsions, preferably oil-in-water emulsions, which comprise an oil phase and an aqueous phase.

A "physiologically acceptable carrier" as defined in the present invention comprises oil phase components and aqueous phase components.

Oil phase components include: branched and unbranched hydrocarbons, for example vaseline oil (petrolatum), paraffin oil, squalane, squalene, polyisobutene and polydecene, preferably vaseline oil, polydecene and squalane; silicone oils, for example, dimethicone, phenyl trimethicone, cyclopentasiloxane and dimethiconol; fatty acids selected from saturated and partially unsaturated fatty acids having from 8 to 20 carbon atoms, for example octanoic (caprylic) acid, nonanoic (pelargonic) acid, decanoic (capric) acid, dodecanoic (lauric) acid, tetradecanoic (myristic) acid, hexadecanoic (palmitic) acid, octadecanoic (stearic) acid, isooctadecanoic (isostearic) acid, cis-9-octadecenoic (oleic) acid, cis-9,12-octadecadienoic (linoleic) acid, eicosanoic (arachidic) acid, docosanoic acid (behenic) and cis-13-docosenoic acid (erucic acids); $C_1$-$C_{20}$ alkyl and alkenyl esters of saturated and partially unsaturated fatty acids having from 10 to 20 carbon atoms, for example decyl oleate, isodecyl oleate, dioctyl maleate, diisopropyl palmitate, isohexyl palmitate, ethyl-hexyl palmitate, lauryl lactate, myristyl lactate, cetyl lactate, isostearyl neopentanoate, ethyl-hexyl isostearate, myristyl myristate, hexyl laurate, isohexyl laurate, isohexyl palmitate, isopropyl palmitate, hexadecyl stearate, decyl stearate, isopropyl isostearate, diisopropyl adipate, diisohexyl adipate, dihexyldecyl adipate, isocetyl stearoyl stearate, $C_{12}$-$C_{15}$ alkyl lactates, and combinations thereof, preferably decyl oleate, ethyl-hexyl palmitate, lauryl lactate; dioctyl maleate, myristyl myristate, isopropyl palmitate, and isostearyl neopentanoate; fatty alcohols, for example lauryl, myristyl, cetyl, hexadecyl, stearyl, isostearyl, hydroxystearyl, oleyl, behenyl, and erucyl alcohols, preferably cetyl alcohol and cetyl-stearyl alcohol; fatty acid triglycerides and mixture thereof, for example caprylic/capric triglyceride.

The oil phase further comprises the glyceryl and polyglyceryl fatty acid esters components of the polyol system as defined above.

Aqueous phase components include water; organic salts, for example sodium citrate, sodium potassium tartrate and disodium ethylenediaminetetraacetic acid (disodium EDTA); inorganic salts such as sodium chloride, sodium metabisulfite, and magnesium sulphate; buffering agents, for example sodium hydroxyde, sodium bicarbonate, zinc carbonate, magnesium carbonate, calcium carbonate, magnesium hydroxide, sodium hydrogen phosphate, calcium acetate, calcium hydroxide, calcium lactate, calcium maleate, calcium oleate and combinations thereof; preservatives, for example glycine lipoderivatives such as e.g., glycine-octanoic acid and glycine-undecylenic acid, essential oils such as, e.g., eucalyptus, tymol, cinnamon and geranium oils, and chlorexidine digluconate; aminoacids, for example arginine and lysine; gelling agents, for example cellulose derivatives, xantan gum, alginates and carragenans, polymers of acrylic acids, for example carbomers and methacrylates derivatives.

The aqueous phase further comprises glycerol, the sugar polyalcohols and the saccharide components of the polyol system as well as NAC.

Preferably, the water used in the present invention is deionised water. The amount of the water used in the preparations of the present invention is relative to the total amount of other components used such that the total weight of the preparation is equal to 100% by weight of topic preparations.

The oil phase is in an amount of from about 25% to about 45% by weight of the total weight of the preparation. Preferably, the oil phase is in an amount of from about 20% to about 30% by weight. The aqueous phase is in an amount of from about 55% to about 85% by weight of the total weight of the preparation. Preferably, the aqueous phase is in an amount of from about 60% to about 70% by weight. The polyol system is present in an amount in the range of from about 0.5% to about 30% by weight of the total weight of the preparation. Preferably the polyol system is in an amount of from about 2% to about 10% by weight. NAC is in an amount of from about 1% to about 15% by weight of the total weight of the preparation. Preferably NAC is in an amount of from about 5% to about 10% by weight.

The preparation of the present invention may comprise, if desired, a wide range of optional components such as, for example fragrances, botanical extracts, sun screens and colouring agents. Such optional components can be added to the preparation after the oil phase and the aqueous phase have been combined or mixed together. Components added to the preparation after the oil and aqueous phases are sufficiently combined are referred to as "post combination components".

A method of preparing a topical application medicament and/or a cosmetic preparation for the treatment of the surface of the skin of a mammal in particular a human, said method comprising blending NAC with a physiologically acceptable carrier, wherein said preparation comprises a polyol system as odour controlling agent, is also encompassed by the present invention.

It is another object of the present invention the use of the preparations according to the invention for treating cosmetic conditions and/or dermatological disorders.

The term "cosmetic conditions" as used herein includes, but it is not limited to, superficial wrinkles and coarse, deep wrinkles, skin lines, sagging, discoloration, age spots and other signs of skin aging, decreasing pore size, providing a skin lightening benefit, irritation of skin due to UV radiation exposure, wind, low humidity, harsh surfactants, abrasives, and the like.

The term "dermatological disorders" as used herein comprises hypercheratosis, xerosis, diseases mediated by proteases, ichtyosis, psoriasis, acne vulgaris and dermal inflammations propagated by leukotriens.

The preparations according to the present invention can be prepared by any method known in the art. In general, such preparatory methods include the step of making the oil phase and the aqueous phase in separate vessels and then combining the oil and aqueous phases.

The oil phase is made by mixing the oil phase components together with constant stirring in a mixing vessel separate from the mixing vessel containing the aqueous phase components, for a time depending on the size of the mixing vessel used, and thus adequate mixing time may range from minutes to hours. If required to allow the melting of solid components, the oil phase can be heated to a temperature of from about 40° C. to about 90° C., preferably from about 60 to about 75° C.

The aqueous phase is made by dissolution of solid and liquid components in water under gently stirring, for a time depending on the size of the mixing vessel used, and thus adequate mixing time may range from minutes to hours. If required to obtain the emulsion, the aqueous phase can be heated to the same temperature of melt oil phase.

The oil phase is then mixed together with the aqueous phase under constant stirring to homogeneity. Mixing of the two phases may occur in the same vessel or tank that the oil phase or aqueous phase is originally mixed in. The resultant mixture is cooled at about room temperature in an appropriate type of known cooling vessel, until the mixture reaches the desired temperature. If desired, a post combination component as defined above may be blended into homogeneity with continued slowed mixing. The mixture may then be stored in a sealed container and then packaged.

All the components of the preparations of the present invention are commercially available compounds or can be easily prepared following procedures well known in the art.

In order to better illustrate the present invention, the following examples are provided. All parts, percentages and proportions referred to here and in the appended claims are by weight (total composition), unless otherwise indicated.

EXAMPLE 1

Preparation A

| Component | weight % of total |
|---|---|
| Oil phase | |
| Vaseline oil | 10% |
| Squalane | 10% |
| Decyl oleate | 5% |
| Polyglyceryl-3-diisostearate | 5% |
| Aqueous phase | |
| Sorbitol | 1% |
| Sodium hydroxide | 1.3% |
| Sodium chloride | 0.5% |
| EDTA disodium salt | 0.01% |
| NAC | 5% |
| Sodium metabisulfite | 0.01% |
| Water | up to 100% |

The method of making Preparation A using the above listed components is now described. The oil phase components were mixed together in a stainless steel container at room temperature, for 15 minutes with constant stirring.

At the same time, the aqueous phase components are mixed together as well. In a separate container, solid components of the aqueous phase were dry-blended together and then slowly sifted into a mixing vortex with deionised water and mixing was continued for about 5 minutes so that, once a homogenous dispersion was obtained, the residual components of the aqueous phase were added.

The oil phase was then added to the aqueous phase with constant stirring for about 15 minutes and the desired emulsion was obtained.

Following analogous procedures, the below listed Preparations W and B were prepared.

Preparation W

| Component | weight % of total |
|---|---|
| Oil phase | |
| Vaseline oil | 10% |
| Squalane | 10% |
| Decyl oleate | 5% |
| Aqueous phase | |
| Sodium hydroxide | 1.3% |
| Sodium chloride | 0.5% |
| EDTA disodium salt | 0.01% |
| NAC | 5% |
| Sodium metabisulfite | 0.01% |
| Water | up to 100% |

Preparation B

| | weight % of total |
|---|---|
| Oil phase | |
| Silicon oil | 5% |
| Caprylic/capric triglyceride | 10% |
| Isopropyl palmitate | 5% |
| Isostearyl neopentanoate | 10% |
| Polyglyceryl-2-diisostearate | 1% |
| Polyglyceryl-3-diisostearate | 2% |
| Aqueous phase | |
| NAC | 5% |
| Sucrose | 2% |
| Dextrose | 0.5% |
| Propylene glycol | 3% |
| Sodium hydroxide | 1.2% |
| Magnesium sulphate | 0.9% |
| EDTA disodium salt | 0.01% |
| Sodium metabisulfite | 0.01% |
| Water | up to 100% |

EXAMPLE 2

Preparation C

| | weight % of total |
|---|---|
| Oil phase | |
| Squalane | 10% |
| Lauryl lactate | 10% |
| Ethyl hexyl palmitate | 5% |
| Polyglyceryl-3-diisostearate | 10% |
| Aqueous phase | |
| NAC | 5% |
| NaOH | to reach pH = 6.3 |
| NaH$_2$PO$_4$ | to reach pH = 6.3 |
| EDTA disodium salt | 0.02% |
| Sodium metabisulfite | 0.01% |
| Xylitol | 3% |
| Perfume | 0.01% |
| Wate | up to 100% |

The method of making Preparation C using the above listed components is now described.

The oil phase components were mixed together in a stainless steel container and heated to a temperature of between 60° to 80° C., for 15 minutes with constant stirring.

At the same time, the aqueous phase components are mixed together as well. In a separate container, solid components of the aqueous phase were dry-blended together and then slowly sifted into a mixing vortex with deionised water and mixing was continued for about 5 minutes so that, once a homogenous dispersion was obtained, the residual components of the aqueous phase were added. The aqueous phase was then heated and heating process was continued until the aqueous phase reached a temperature of between 60° to 80° C.

When both the aqueous phase and the oil phase reached temperature of between 60° to 80° C., the oil phase was added to the aqueous phase with constant stirring for about 15 minutes. The obtained emulsion was then cooled under stirring until room temperature was reached.

Following analogous procedures, the below listed Preparations D-G were prepared.

Preparation D

| | weight % of total |
|---|---|
| Oil phase | |
| Squalane | 10% |
| Dioctyl maleate | 5% |
| Silicon oil | 10% |
| Polyglyceryl-3-diisostearate | 8% |
| Aqueous phase | |
| NAC | 5% |
| NaOH | to reach pH = 6.3 |
| NaH$_2$PO$_4$ | to reach pH = 6.3 |
| EDTA disodium salt | 0.02% |
| Sodium metabisulfite | 0.01% |
| Xylitol | 3% |
| Perfume | 0.01% |
| Water | up to 100% |

Preparation E

| | weight % of total |
|---|---|
| Oil phase | |
| Polydecene | 12% |
| Stearic acid | 4% |
| Ethyl hexyl palmitate | 8% |
| Polyglyceryl-2-diisostearate | 10% |
| Aqueous phase | |
| NAC | 10% |
| Xylitol | 3% |
| Sodium hydroxide | 2.5% |
| Magnesium sulphate | 1% |
| EDTA disodium salt | 0.01% |
| Sodium metabisulfite | 0.01% |
| Water | up to 100% |

Preparation F

| | weight % of total |
|---|---|
| Oil phase | |
| Dioctyl maleate | 9% |
| Polyisobutene | 2% |
| Cetyl-stearyl alcohol | 4% |
| Myristyl myristate | 15% |
| Polyglyceryl-2-diisostearate | 3% |
| Polyglyceryl-3-diisostearate | 6% |
| Aqueous phase | |
| N-acetylcysteine | 7% |
| Mannitol | 2% |
| Lactose | 0.5% |
| Glycerol | 3% |
| Sodium hydroxide | 1.8% |
| Magnesium sulphate | 0.3% |
| EDTA disodium salt | 0.01% |
| Sodium metabisulfite | 0.01% |
| Water | up to 100% |

Preparation G

| | weight % of total |
|---|---|
| Oil phase | |
| Glyceryl monostearate | 6% |
| Cetylic alcohol | 4% |
| Vaseline oil | 12% |
| Polyglyceryl-3-diisostearate | 6% |
| Aqueous phase | |
| N-acetylcysteine | 5% |
| Xylitol | 2% |
| Maltodextrines | 2% |
| Hydroxypropylmethylcellulose | 0.5% |
| Sodium hydroxide | 1.2% |
| Sodium chloride | 0.5% |
| EDTA disodium salt | 0.01% |
| Sodium metabisulfite | 0.01% |
| Water | up to 100% |

EXAMPLE 3

In order to demonstrate the malodour controlling activity of the polyol system, it was carried out a test using the Preparation A of Example 1, namely the preparation containing the malodour controlling polyol system and Preparation W of Example 1, namely the corresponding preparation without said system.

Subjective odour assessment was made by 10 different assessors after applying the preparation on the hand skin surface, 10 minutes after application.

The assessors adopted a malodour intensity control value of 5 for the Preparation W.

The results of assessment obtained with Preparation A are reported in the following table.

| Assessor | Malodour intensity |
|---|---|
| 1 | 1 |
| 2 | 1 |
| 3 | 1 |
| 4 | 2 |
| 5 | 1 |
| 6 | 1 |
| 7 | 2 |
| 8 | 1 |
| 9 | 1 |
| 10 | 1 |

The invention claimed is:

1. An odor-improved dermatological or cosmetic preparation for topical use, which preparation is an oil-in-water emulsion comprising N-acetylcysteine (NAC), a physiologically acceptable carrier, and a polyol system for controlling odor; wherein the polyol system comprises:
 (1) at least one component selected from the group consisting of glyceryl fatty acid esters and polyglyceryl fatty acid esters in the oil phase of the emulsion, wherein the polyglyceryl fatty acid esters comprise polyglycerols having a degree of polymerization ranging from 3 to 10 partially esterified with fatty acids selected from saturated and partially unsaturated fatty acids having a carbon number from 8 to 20 selected from the group consisting of octanoic (caprylic) acid, nonanoic (pelargonic) acid, decanoic (capric) acid, dodecanoic (lauric) acid, tetradecanoic (myristic) acid, hexadecanoic (palmitic) acid, octadecanoic (stearic) acid, isooctadecanoic (isostearic) acid, cis-9-octadecanoic (oleic) acid, cis-9,12-octadecanoic (linoleic) acid, eicosanoic (arachidic) acid, docosanoic acid (behenic) and cis-13-docosenoic acid (erucic acids);and (2) at least one component selected from the group consisting of glycerol, sugar polyalcohols, and saccharides in the aqueous phase of the emulsion.

2. The preparation according to claim 1, wherein the glyceryl fatty acid esters and the polyglyceryl fatty acid esters are monoesterified.

3. The preparation according to claim 1, wherein the glyceryl fatty acid esters comprise glycerol partially esterified with a fatty acid having a carbon number from 8 to 22 selected from the group consisting of octanoic (caprylic) acid, pelargonic acid, decanoic (capric) acid, dodecanoic (lauric) acid, myristic acid, palmitic acid, stearic acid, isostearic acid, oleic acid and linoleic acid.

4. The preparation according to claim 1, wherein the polyglyceryl fatty acid esters have a degree of polymerization ranging from 3 to 6 and are monoesterified.

5. The preparation according to claim 1, wherein the sugar polyalcohols comprise at least one member selected from the group consisting of erythritol, xylitol, mannitol and sorbitol.

6. The preparation according to claim 1, wherein the saccharides comprise at least one member selected from the group consisting of dextrose, sucrose, lactose and maltodextrins.

7. The preparation according to claim 1, which further comprises at least one additive selected from the group consisting of fragrances, botanical extracts, sun screens and colouring agents.

8. The preparation according to claim 1, wherein the emulsion is an oil-in-water emulsion comprising an oil phase and an aqueous phase.

9. A medicament for the treatment of dermatological disorders comprising a preparation according to claim 1.

10. The medicament according to claim 9, wherein the dermatological disorders are selected from the group consisting of hypercheratosis, xerosis, diseases mediated by proteases, ichtyosis, psoriasis, acne vulgaris and dermal inflammations propagated by leukotrienes.

11. The preparation according to claim 1, for use in treating cosmetic conditions.

12. The preparation according to claim 11, wherein the cosmetic conditions are selected from the group consisting of superficial wrinkles and coarse, deep wrinkles, skin lines, sagging, discoloration, age spots, decreasing pore size, and irritation of the skin due to UV radiation exposure, wind, low humidity, surfactants, or abrasives.

13. A method of preparing a an odor-improved topical application medicament and/or a cosmetic preparation for the treatment of the surface of the skin of a mammal, said method comprising blending (1) an oil composition comprising a physiologically acceptable carrier and at least one component selected from the group consisting of glyceryl fatty acid esters and polyglyceryl fatty acid esters, with (2) an aqueous composition comprising N-acetylcysteine (NAC) and at least one component selected from the group consisting of glycerol, sugar polyalcohols, and saccharides.

* * * * *